(12) United States Patent
Sato et al.

(10) Patent No.: US 10,308,672 B2
(45) Date of Patent: Jun. 4, 2019

(54) METHOD FOR PRODUCING MONOMER FOR SINGLE-STRANDED NUCLEIC ACID MOLECULE

(71) Applicant: SUMITOMO CHEMICAL COMPANY, LIMITED, Tokyo (JP)

(72) Inventors: Kanako Sato, Osaka (JP); Hideki Ihara, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/085,330

(22) PCT Filed: Apr. 17, 2017

(86) PCT No.: PCT/JP2017/015435
§ 371 (c)(1),
(2) Date: Sep. 14, 2018

(87) PCT Pub. No.: WO2017/188042
PCT Pub. Date: Nov. 2, 2017

(65) Prior Publication Data
US 2019/0100540 A1    Apr. 4, 2019

(30) Foreign Application Priority Data
Apr. 26, 2016 (JP) .................. 2016-087783

(51) Int. Cl.
*C07F 9/572* (2006.01)
*C12N 15/113* (2010.01)

(52) U.S. Cl.
CPC ............ *C07F 9/572* (2013.01); *C12N 15/113* (2013.01); *C12N 2330/30* (2013.01)

(58) Field of Classification Search
CPC .... C07F 9/572; C12N 15/113; C12N 2330/30
(Continued)

(56) References Cited

U.S. PATENT DOCUMENTS

| 2012/0035246 A1 | 2/2012 | Ohgi et al. |
| 2014/0206856 A1 | 7/2014 | Aoki et al. |

(Continued)

FOREIGN PATENT DOCUMENTS

| JP | 2013-055913 A | 3/2013 |
| WO | WO 2013/077446 A1 | 5/2013 |

OTHER PUBLICATIONS

International Search Report for PCT/JP2017/015435 (PCT/ISA/210) dated Jul. 4, 2017.

*Primary Examiner* — Kristin A Vajda
(74) *Attorney, Agent, or Firm* — Birch, Stewart, Kolasch & Birch, LLP

(57) ABSTRACT

A compound represented by formula (3):

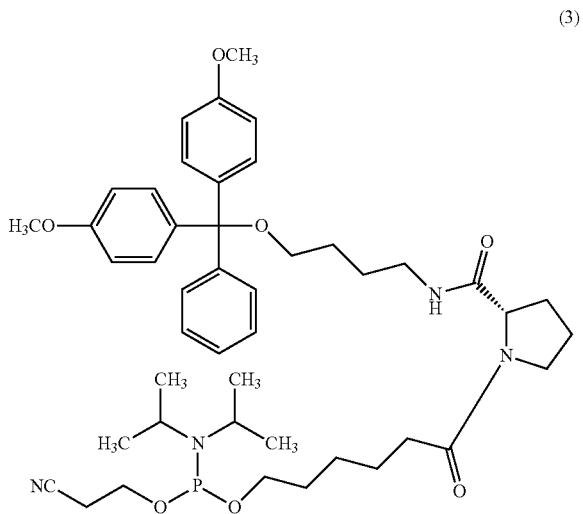

(3)

or an enantiomer thereof can be obtained by comprising: reacting a compound represented by formula (1):

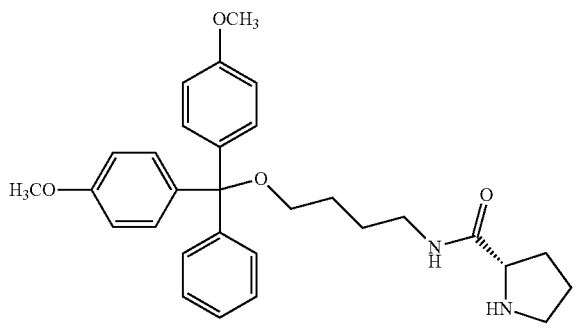

(1)

or an enantiomer thereof with 6-hydroxyhexanoic acid in a solvent in the presence of an additive such as 1-hydroxybenzotriazole and a condensing agent, and then mixing the resultant reaction mixture, water, and a base such as alkali metal hydroxide to produce a compound represented by formula (2):

(Continued)

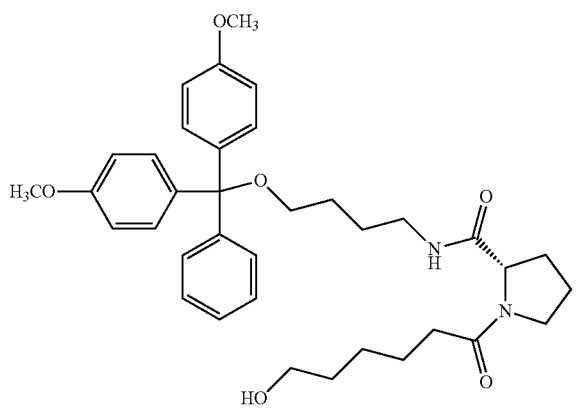

(2)

or an enantiomer thereof; and reacting the compound represented by formula (2) or an enantiomer thereof with 2-cyanoethyl-N,N,N',N'-tetraisopropylphosphorodiamidite in a solvent in the presence of a coupling activator.

5 Claims, No Drawings

(58) Field of Classification Search
USPC .......................................................... 548/413
See application file for complete search history.

(56) References Cited

U.S. PATENT DOCUMENTS

| | | |
|---|---|---|
| 2015/0106443 A1 | 4/2015 | Ohgi et al. |
| 2016/0376589 A1 | 12/2016 | Ohgi et al. |

METHOD FOR PRODUCING MONOMER FOR SINGLE-STRANDED NUCLEIC ACID MOLECULE

TECHNICAL FIELD

The present invention relates to a method for producing a monomer used for producing a single-stranded nucleic acid molecule capable of suppressing the expression of a target gene.

BACKGROUND ART

US2012/0035246 discloses a method for producing a single-stranded nucleic acid molecule capable of suppressing the expression of a target gene, and, as a monomer used for its production, production of a compound represented by formula (3)

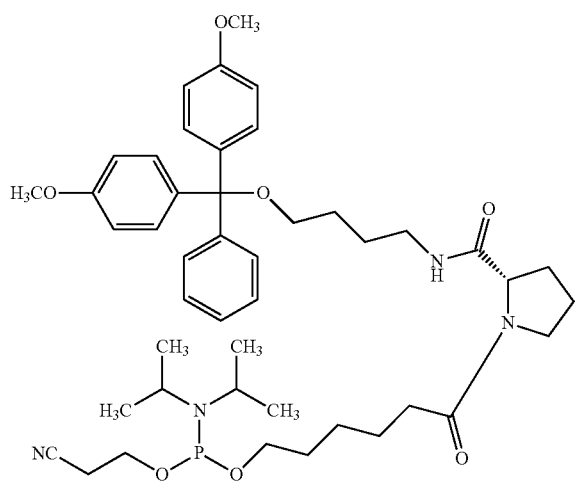

(3)

(hereinafter referred to as the compound (3)) and its enantiomer is described in Example A3.

However, when the compound (3) obtained by the method described in US2012/0035246 is used, the yield of the single-stranded nucleic acid molecule is not necessarily sufficient.

SUMMARY OF THE INVENTION

The present invention provides a method for producing the compound (3) capable of producing the single-stranded nucleic acid molecule with high yield.

The present invention is as follows.

[1] A method for producing a compound (3) or an enantiomer thereof, comprising:

reacting a compound represented by formula (1):

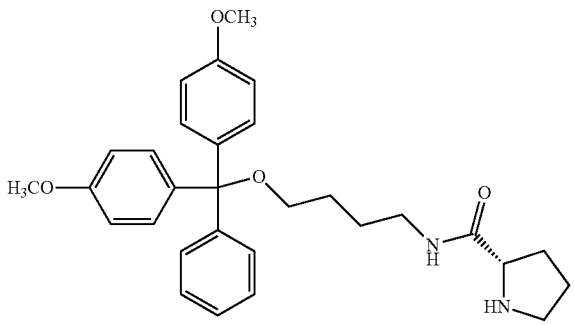

(1)

hereinafter referred to as the compound (1)) or an enantiomer thereof with 6-hydroxyhexanoic acid in a solvent in the presence of an additive and a condensing agent selected from the group consisting of 1-hydroxybenzotriazole, 1-hydroxy-7-azabenzotriazole, N-hydroxysuccinimide, ethyl(hydroxyimino)cyanoacetate, N,N'-disuccinimidyl carbonate, N-hydroxyphthalimide, N-hydroxypiperidine, 3-hydroxy-4-oxo-3,4-dihydro-1,2,3-benzotriazine and N-hydroxy-5-norbornene-2,3-dicarboxylic acid imide, and then mixing the resultant reaction mixture, water, and a base selected from the group consisting of alkali metal hydroxide, alkali metal carbonate, a bicyclic amidine compound, alkali metal alkoxide, and quaternary ammonium hydroxide to produce a compound represented by formula (2):

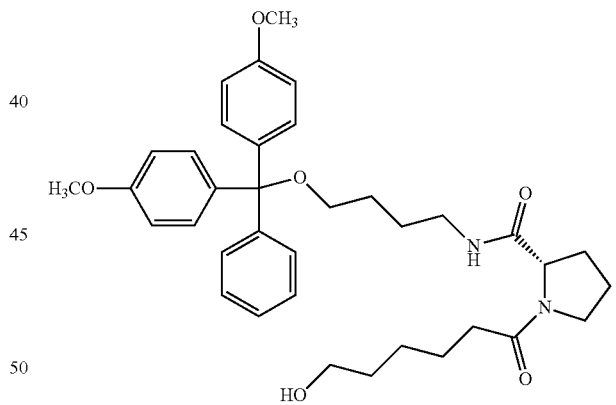

(2)

(hereinafter referred to as the compound (2)) or an enantiomer thereof; and reacting the compound represented by formula (2) and obtained in the production step or an enantiomer thereof with 2-cyanoethyl-N,N,N',N'-tetraisopropylphosphorodiamidite in a solvent in the presence of a coupling activator to obtain the compound (3) or an enantiomer thereof.

[2] The production method according to [1], wherein the base is an alkali metal hydroxide.

[3] The production method according to [1] or [2], wherein the condensing agent is 1-ethyl-3-(3-dimethylaminopropyl)carbodiimide hydrochloride, 1-ethyl-3-(3-dimethylaminopropyl)carbodiimide, N,N'-dicyclohexylcarbodiimide, N,N'-diisopropylcarbodiimide, 1,1-carbonyldiimidazole, 1-propylphosphonic anhydride cyclic trimer or 2-chloro-4,6-dimethoxy-1,3,5-triazine.

[4] The production method according to any one of [1] to [3], wherein the additive is 1-hydroxybenzotriazole, 1-hydroxy-7-azabenzotriazole, N-hydroxysuccinimide, ethyl(hydroxyimino)cyanoacetate or N,N'-disuccinimidyl carbonate.

[5] The production method according to any one of [1] to [4], wherein the coupling activator is diisopropylaminetetrazole salt, 1H-tetrazole, 5-(ethylthio)-1H-tetrazole, 5-(benzylthio)-1H-tetrazole or 4,5-dicyanoimidazole.

MODE FOR CARRYING OUT THE INVENTION

A compound (1) used in the production method of the present invention can be obtained by the method described in US2012/0035246. More specifically, the compound (1) can be obtained in Reference Example 4 described later.

There will be described a process for producing a compound (2) by reacting a compound (1) with 6-hydroxyhexanoic acid in a solvent in the presence of an additive and a condensing agent selected from the group consisting of 1-hydroxybenzotriazole, 1-hydroxy-7-azabenzotriazole, N-hydroxysuccinimide, ethyl (hydroxyimino)cyanoacetate, N,N'-disuccinimidyl carbonate, N-hydroxyphthalimide, N-hydroxypiperidine, 3-hydroxy-4-oxo-3,4-dihydro-1,2,3-benzotriazine and N-hydroxy-5-norbornene-2,3-dicarboxylic acid imide, and then mixing the resultant reaction mixture, water, and a base selected from the group consisting of alkali metal hydroxide, alkali metal carbonate, a bicyclic amidine compound, alkali metal alkoxide, and quaternary ammonium hydroxide.

As the solvent, a solvent inert to the dehydration condensation reaction is used, and examples thereof include halogenated hydrocarbons such as dichloromethane and chloroform, aromatic hydrocarbons such as toluene and xylene, ethers such as tetrahydrofuran, 2-methyltetrahydrofuran, methyl tert-butyl ether, cyclopentyl methyl ether, 1,4-dioxane and diethyl ether, ketones such as acetone, 2-butanone and methyl isobutyl ketone, esters such as methyl acetate and ethyl acetate, amides such as dimethyl formamide, dimethyl acetamide, and N-methyl pyrrolidone, ureas such as 1,3-dimethyl-2-imidazolidinone and N,N'-dimethylpropylene urea, nitriles such as acetonitrile and propionitrile, and sulfur-containing compounds such as dimethyl sulfoxide and sulfolane. The amount of the solvent to be used is generally 0.5 to 100 times by weight of the compound (1).

As the condensing agent, a condensing agent used for the dehydration condensation reaction is used, and examples thereof include 1-ethyl-3-(3-dimethylaminopropyl)carbodiimide hydrochloride, 1-ethyl-3-(3-dimethylaminopropyl)carbodiimide, N,N'-dicyclohexylcarbodiimide, N,N'-diisopropylcarbodiimide, 1,1-carbonyldiimidazole, 1-propylphosphonic anhydride cyclic trimer and 2-chloro-4,6-dimethoxy-1,3,5-triazine.

For the reaction, per 1 mol of the compound (1), the additive is generally used in a ratio of 0.1 mol to 20 mols, and the condensing agent is generally used in a ratio of 1 mol to 10 mols.

A tertiary amine may be added for the reaction. Examples of the tertiary amine include triethylamine and diisopropylethylamine. The amount of the tertiary amine to be added is generally 0.1 to 30 mol per 1 mol of the compound (1).

When a solvent having a boiling point of 70° C. or more is used, the reaction temperature is usually in the range of 10° C. to 70° C., and when a solvent having a boiling point of less than 70° C. is used, the reaction temperature is usually in the range of 10° C. to the reflux temperature of the solvent.

The reaction time is usually 0.5 hour to 150 hours.

After the reaction, when the solvent is mixed with water and a base, usually the solvent is distilled off to perform concentration. Another solvent may be added to the residue obtained by distilling off the solvent and then mixed with water and a base.

In the case of using ethers, amides, ureas or nitriles as a solvent, the resultant reaction mixture, as it is or after concentrated by distilling off the solvent, is mixed with water and a base selected from the group consisting of alkali metal hydroxide, alkali metal carbonate, bicyclic amidine compound, alkali metal alkoxide, and quaternary ammonium hydroxide. In the case of using halogenated hydrocarbons, aromatic hydrocarbons, esters, ketones or sulfur-containing compounds as a solvent, a residue concentrated by distilling off the solvent of the resultant reaction mixture is diluted with ethers, amides, ureas, or nitriles and then mixed with water and a base selected from the group consisting of alkali metal hydroxide, alkali metal carbonate, bicyclic amidine compound, alkali metal alkoxide, and quaternary ammonium hydroxide.

Examples of the alkali metal hydroxide include lithium hydroxide, sodium hydroxide and potassium hydroxide.

Examples of the alkali metal carbonate include sodium carbonate, potassium carbonate and cesium carbonate.

Examples of the bicyclic amidine compound include diazabicycloundecene and diazabicyclononene.

Examples of the alkali metal alkoxide include sodium methoxide and potassium tert-butoxide.

Examples of the quaternary ammonium hydroxide include benzyltrimethylammonium hydroxide, triethylmethylammonium hydroxide and tributylmethylammonium hydroxide.

The amount of the base to be used is generally 0.1 to 10 mol per 1 mol of the compound (1).

The amount of water to be used is generally 0.1 to 10 times by weight of the compound (1).

The mixing order of the compound (1), water and the base is not limited, and the base and water may be first mixed and then mixed with the compound (1).

The mixture is usually held for 0.5 to 150 hours.

When a solvent having a boiling point of 70° C. or more is used, the mixture is usually held in the range of 10° C. to 70° C., and when a solvent having a boiling point of less than 70° C. is used, the mixture is usually held in the range of 10° C. to the reflux temperature of the solvent.

Thereafter, the compound (2) can be isolated by extraction with an organic solvent and concentration.

Next, there will be described a process of obtaining a compound (3) by reacting the obtained compound (2) with 2-cyanoethyl-N,N,N',N'-tetraisopropylphosphorodiamidite in an inert solvent in the presence of a coupling activator.

Examples of the solvent include halogenated hydrocarbons such as dichloromethane and chloroform, aromatic hydrocarbons such as toluene and xylene, ethers such as tetrahydrofuran, 2-methyltetrahydrofuran, methyl tert-butyl ether, cyclopentyl methyl ether, 1,4-dioxane and diethyl ether, ketones such as acetone, 2-butanone and methyl isobutyl ketone, esters such as methyl acetate and ethyl acetate, amides such as dimethylformamide, dimethylacetamide, and N-methylpyrrolidone, ureas such as 1,3-dimethyl-2-imidazolidinone and N,N'-dimethylpropylene urea, nitriles such as acetonitrile and propionitrile, and sulfur-containing compounds such as dimethyl sulfoxide and sulfolane. The amount of the solvent to be used is generally 0.5 to 100 times by weight of the compound (2).

The coupling activator means a coupling activator used for oligonucleotide synthesis by a phosphoramidite method and is described in Tetrahedron, 69, 2013, 3615-3637, for example. Specific examples of the coupling activator include the following (i), (ii) and (iii):

(i) azole coupling activator 1H-tetrazole;

modified tetrazole coupling activators such as 5-(4-nitrophenyl)-1H-tetrazole, 5-(bis-3,5-trifluoromethylphenyl)-1H-tetrazole, 5-ethylthio-1H-tetrazole, 5-benzylthio-1H-tetrazole, 5-methylthio-1H-tetrazole and 5-mercapto-1H-tetrazole;

imidazole coupling activators such as 4,5-dicyanoimidazole, 2-bromo-4,5-dicyanoimidazole, 2-benzyl-4,5-dicyanoimidazole, and 2-bromo-4,5-diethyl-carboxylimidazole;

1-hydroxybenzotriazole coupling activators such as 1-hydroxy-benzotriazole, 6-trifluoromethyl-1-hydroxy-benzotriazole, and 4-nitro-1-hydroxy-benzotriazole;

3-nitrotriazole coupling activator such as 3-nitrotriazole;

(ii) salt complex coupling activator pyridinium salt complex coupling activators such as pyridine hydrochloride and pyridine trifluoroacetate salt;

azolium salt complex coupling activators such as benzimidazole trifluoroacetate and N-phenylimidazole trifluoroacetate;

saccharin salt complex coupling activator such as saccharin-1-methyl imidazole salt;

ammonium salt complex coupling activators such as dialkyl(cyanomethyl)ammonium tetrafluoroborate and diisopropylaminetetrazole salt;

(iii) other coupling activators used for oligonucleic acid synthesis by phospheramidite method carboxylic acid coupling activators such as trichloroacetic acid, trifluoroacetic acid, dichloroacetic acid, and 2,4-dinitrobenzoic acid;

Lewis acid coupling activators such as iron chloride (III), aluminum chloride (III), boron trifluoride diethyl ether complex, zirconium chloride (IV), and bismuth chloride (III);

trimethylchlorosilane;

2,4-dinitrophenol;

For the reaction, per 1 mol of the compound (2), 2-cyanoethyl-N,N,N',N'-tetraisopropylphosphorodiamidite is generally used in a ratio of 1 mol to 10 mols, and the coupling activator is generally used in a ratio of 0.1 mol to 10 mols.

When a solvent having a boiling point of 70° C. or more is used, the reaction temperature is usually in the range of 10° C. to 70° C., and when a solvent having a boiling point of less than 70° C. is used, the reaction temperature is usually in the range of 10° C. to the reflux temperature of the solvent. The reaction time is usually 0.3 hour to 150 hours.

After completion of the reaction, an organic layer is concentrated after washing with saturated sodium bicarbonate water or the like, whereby the compound (3) can be isolated.

The obtained compound (3) can be purified by chromatography or the like.

A single-stranded nucleic acid molecule can be produced using the compound (3) based on a phosphoramidite method.

The method for producing the compound (3) can be applied to an enantiomer of the compound (3). An enantiomer of the compound (1) as a starting material can be easily prepared from commercially available raw materials in the same manner as the compound (1). The enantiomer of the compound (3) is also useful, as described in US2012/0035246.

EXAMPLES

Example 1

16.94 mmol (3.28 g) of the compound (1), 20.33 mmol (3.90 g) of 1-ethyl-3-(3-dimethylaminopropyl)carbodiimide hydrochloride, 40.62 mmol (6.22 g) of 1-hydroxybenzotriazole, 61.00 mmol (8.50 ml) of triethylamine, and anhydrous dichloromethane (160 mL) were mixed. 20.0 mmol (2.64 g) of 6-hydroxyhexanoic acid was further added to the resultant mixture at room temperature under a nitrogen atmosphere, followed by stirring at room temperature for 3 hours under a nitrogen atmosphere. The resultant mixture was diluted with 800 mL of dichloromethane and washed three times with 1000 mL of saturated brine. The resultant organic layer was dried over sodium sulfate, and a solvent was then distilled off under reduced pressure to obtain 10.40 g of a residue.

5.20 g of the obtained residue, 10.4 mL of tetrahydrofuran and 5.2 ml of water were mixed, 17.25 mmol (0.72 g) of lithium hydroxide monohydrate was added thereto, and the mixture was stirred at 40° C. to 50° C. for 6 hours. The resultant mixture was allowed to cool to room temperature, 26 ml of toluene and 52 mL of water were then added, and the mixture was stirred at room temperature for 15 minutes. The organic layer collected by separation was washed twice with sodium bicarbonate water (a mixture of 2.76 g of sodium hydrogencarbonate and 52 mL of water), and the solvent was distilled off under reduced pressure. The residue was dissolved in 31.2 mL of acetonitrile, and the solvent was then distilled off under reduced pressure to obtain the compound (2) (purity: 93%, yield: 85%).

7.13 mmol (4.30 g) of the obtained compound (2) was mixed with anhydrous acetonitrile and subjected to azeotropic dehydration three times at room temperature. 8.53 mmol (1.46 g) of diisopropylaminetetrazole salt was added to the resultant residue, degassed under reduced pressure, and then charged with nitrogen gas. 5 mL of anhydrous acetonitrile was added to the resultant mixture, and, in addition, 3.5 mL of an anhydrous acetonitrile solution of 8.56 mmol (2.58 g) of 2-cyanoethyl-N,N,N',N'-tetraisopropylphosphorodiamidite was added. The mixture was stirred at room temperature under a nitrogen atmosphere for 2 hours. The resultant mixture was diluted with 50 mL of dichloromethane, washed three times with 100 mL of saturated sodium bicarbonate water, and then washed with 100 mL of saturated brine. The resultant organic layer was dried over sodium sulfate, and the solvent was then distilled off under reduced pressure. The resultant residue was subjected to column chromatography using amino silica gel as a filler (eluent hexane:ethyl acetate=1:3, 0.05% pyridine-containing) to give the compound (3) (yield: 82.4%).

Example 2

2.83 g of 1-ethyl-3-(3-dimethylaminopxopyl) carbodiimide hydrochloride, 4.51 g of 1-hydroxybenzotriazole and 4.47 g of triethylamine were added to a mixture of 6.00 g of the compound (1) obtained by the method described in Reference Example 4 and 120 mL of chloroform. 1.95 g of 6-hydroxyhexanoic acid was added to the resultant mixture, and the mixture was stirred at room temperature for 3 hours under a nitrogen atmosphere. The resultant mixture was diluted with chloroform and washed three times with a 5% aqueous sodium chloride solution. A solvent of an organic layer was distilled off under reduced pressure. 15 mL of tetrahydrofuran was added to the residue, and a mixture of 0.59 g of lithium hydroxide and 7.4 mL of water was then added. After the resultant mixture was stirred at room temperature for 22 hours, toluene was added, and the mixture was washed with water to obtain an organic layer. The organic layer was washed three times with a 5% aqueous sodium hydrogen carbonate solution, and the solvent was then distilled off under reduced pressure. The residue was mixed with acetonitrile, and the solvent was distilled off again under reduced pressure, thus obtaining 25.80 g of the compound (2).

After 30 mL of acetonitrile was added to 20.64 g of the obtained compound (2), 2.02 g of diisopropylaminetetrazole salt and 3.55 g of 2-cyanoethyl-N,N,N',N'-tetraisopropylphosphorodiamidite were added, and the mixture was stirred at room temperature for 1 hour under a nitrogen atmosphere. After completion of the reaction, the resultant mixture was diluted with toluene and washed three times with a 5% aqueous sodium hydrogen carbonate solution. The resultant organic layer was dried over magnesium sulfate, and the solvent was then distilled off under reduced pressure. A portion of the resultant residue was subjected to column chromatography using silica gel treated with triethylamine (eluent heptane:ethyl acetate=50:50) to give the compound (3).

Example 3

9.42 g of 1-ethyl-3-(3-dimethylaminopropyl) carbodiimide hydrochloride, 15.04 g of 1-hydroxybenzotriazole and 14.91 g of triethylamine were added to a mixture of 20.00 g of the compound (1) and 200 mL of chloroform. 6.49 g of 6-hydroxyhexanoic acid was added to the resultant mixture, and the mixture was stirred at room temperature for 3 hours under a nitrogen atmosphere. The resultant mixture was diluted with chloroform and washed three times with a 5% aqueous sodium chloride solution. A solvent of an organic layer was distilled off under reduced pressure to obtain 29.87 g of a residue. 10 mL of acetonitrile was added to 4.98 g of the residue, and a mixture of 0.55 g of sodium hydroxide and 5.0 mL of water was then added. After the resultant mixture was stirred at 30° C. for 18 hours, toluene was added, and the mixture was washed with water to obtain an organic layer. The organic layer was washed twice with a 5% aqueous sodium hydrogen carbonate solution, and the solvent was then distilled off under reduced pressure. The residue was mixed with acetonitrile, and the solvent was distilled off again under reduced pressure, thus obtaining 5.03 g of the compound (2).

After 21 mL of acetonitrile was added to 5.03 g of the obtained compound (2), 1.40 g of diisopropylaminetetrazole salt and 2.47 g of 2-cyanoethyl-N,N,N',N'-tetraisopropylphosphorodiamidite were added, and the mixture was stirred at room temperature for 1.5 hour under a nitrogen atmosphere. The resultant mixture was diluted with toluene and washed three times with a 5% aqueous sodium hydrogen carbonate solution. The organic layer was dried over magnesium sulfate, and the solvent was then distilled off under reduced pressure. A portion of the resultant residue was subjected to column chromatography using silica gel treated with triethylamine (eluent heptane:etnyl acetate:triethylamine=40:60:10) to give the compound (3).

Example 4

9.42 g of 1-ethyl-3-(3-dimethylaminopropyl) carbodiimide hydrochloride, 15.04 g of 1-hydroxybenzotriazole and 14.91 g of triethylamine were added to a mixture of 20.00 g of the compound (1) and 200 mL of chloroform. 6.49 g of 6-hydroxyhexanoic acid was added to the resultant mixture, and the mixture was stirred at room temperature for 3 hours under a nitrogen atmosphere. The resultant mixture was diluted with chloroform and washed three times with a 5% aqueous sodium chloride solution. A solvent of an organic layer was distilled off under reduced pressure to obtain 29.87 g of a residue. 10 mL of tetrahydrofuran was added to 4.98 g of the residue, and a mixture of 2.08 g of diazabicycloundecene and 1.0 mL of water was then added. After the resultant mixture was stirred at 50° C. for 1872 hours, toluene was added, and the mixture was washed with water to obtain an organic layer. The organic layer was washed twice with a 5% aqueous sodium hydrogen carbonate solution, and the solvent was then distilled off under reduced pressure. The residue was mixed with acetonitrile, and the solvent was distilled off again under reduced pressure, thus obtaining 8.78 g of the compound (2). After 21 mL of acetonitrile was added to 5.03 g of the obtained compound (2), 1.40 g of diisopropylaminetetrazole salt and 2.47 g of 2-cyanoethyl-N,N,N',N'-tetraisopropylphosphorodiamidite were added, and the mixture was stirred at room temperature for 1.5 hour under a nitrogen atmosphere. The resultant mixture was diluted with toluene and washed three times with a 5% aqueous sodium hydrogen carbonate solution. The organic layer was dried over magnesium sulfate, and the solvent was then distilled off under reduced pressure. A portion of the resultant residue was subjected to column chromatography using silica gel treated with triethylamine (eluent heptane:ethyl acetate:triethylamine=40:60:10) to give the compound (3).

Example 5

9.42 g of 1-ethyl-3-(3-dimethylaminopropyl) carbodiimide hydrochloride, 15.04 g of 1-hydroxybenzotriazole and 14.91 g of triethylamine were added to a mixture of 20.00 g of the compound (1) and 200 mL of chloroform. 6.49 g of 6-hydroxyhexanoic acid was added to the resultant mixture, and the mixture was stirred at room temperature for 3 hours under a nitrogen atmosphere. The resultant mixture was diluted with chloroform and washed three times with a 5% aqueous sodium chloride solution. A solvent of an organic layer was distilled off under reduced pressure to obtain 29.87 g of a residue. 10 mL of tetrahydrofuran was added to 4.98 g of the residue, and a mixture of 1.53 g of potassium tert-butoxide and 5.0 mL of water was then added. After the resultant mixture was stirred at 30° C. for 22 hours, toluene was added, and the mixture was washed with water to obtain an organic layer. The organic layer was washed twice with a 5% aqueous sodium hydrogen carbonate solution, and the solvent was then distilled off under reduced pressure. The residue was mixed with acetonetrile, and the solvent was distilled off again under reduced pressure, thus obtaining 4.78 g of the compound (2).

After 21 mL of acetonitrile was added to 4.78 g of the obtained compound (2), 1.40 g of diisopropylaminetetrazole salt and 2.47 g of 2-cyanoethyl-N,N,N',N'-tetraisopropylphosphorodiamidite were added, and the mixture was stirred at room temperature for 1.5 hour under a nitrogen atmosphere. After completion of the reaction, the resultant mixture was diluted with toluene and washed three times with a 5% aqueous sodium hydrogen carbonate solution. The resultant organic layer was dried over magnesium sulfate, and the solvent was then distilled off under reduced pressure. A portion of the resultant residue was subjected to column chromatography using silica gel treated with triethylamine (eluent heptane:ethyl acetate:triethylamine=40:60:10) to give the compound (3).

Example 6

9.42 g of 1-ethyl-3-(3-dimethylaminopropyl) carbodiimide hydrochloride, 15.04 g of 1-hydroxybenzotriazole and 14.91 g of triethylamine were added to a mixture of 20.00 g of the compound (1) and 200 mL of chloroform. 6.49 g of 6-hydroxyhexanoic acid was added to the resultant mixture, and the mixture was stirred at room temperature for 3 hours under a nitrogen atmosphere. The resultant mixture was diluted with chloroform and washed three times with a 5% aqueous sodium chloride solution. The solvent of the resultant organic layer was distilled off under reduced pressure to obtain 29.87 g of a residue. 10 mL of tetrahydrofuran was added to 4.98 g of the residue, and a mixture of 5.70 g of benzyltrimethylammonium hydroxide aqueous solution (40 wt %) and 1.6 mL of water was then added. After the resultant mixture was stirred at 30° C. for 6 hours, toluene was added, and the mixture was washed with water to obtain an organic layer. The organic layer was washed twice with a aqueous sodium hydrogen carbonate solution, and the solvent was then distilled off under reduced pressure. The residue was mixed with acetonitrile, and the solvent was distilled off again under reduced pressure, thus obtaining 10.21 g of the compound (2).

After 21 mL of acetonitrile was added to 10.21 g of the obtained compound (2), 1.40 g of diisopropylaminetetrazole salt and 2.47 g of 2-cyanoethyl-N,N,N',N'-tetraisopropylphosphorodiamidite were added, and the mixture was stirred at room temperature for 1.5 hour under a nitrogen atmosphere. The resultant mixture was diluted with toluene and washed three times with a 5% aqueous sodium hydrogen carbonate solution. The organic layer was dried over magnesium sulfate, and the solvent was then distilled off under reduced pressure. A portion of the resultant residue was subjected to column chromatography using silica gel treated with triethylamine (eluent heptane:ethyl acetate:triethylamine=40:60:10) to give the compound (3).

Reference Example 1

Using the compound (3) produced in Example 1, a single-stranded nucleic acid molecule (a nucleic acid molecule represented by formula (A):

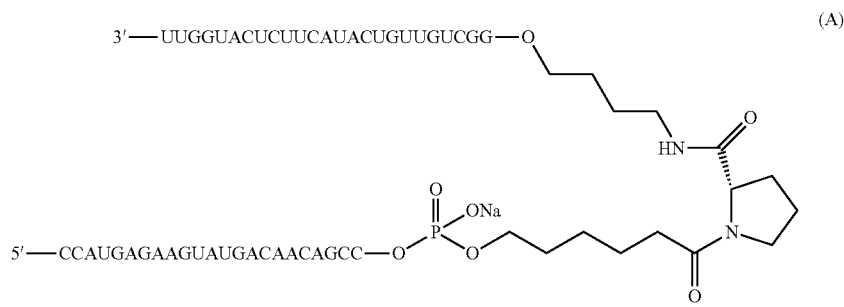

(wherein C means cytidine monophosphate sodium salt, A means adenosine monophosphate sodium salt, U means uridine monophosphate sodium salt, and G means guanosine monophosphate sodium salt); hereinafter referred to as the compound (A)) described in Example (B1) of US2012/0035246 was produced.

Synthesis was performed from the 3' side toward the 5' side using NTS M-4MX-E (manufactured by Nihon Techno Service Co., Ltd.) as a nucleic acid synthesiser. For the synthesis, the uridine EMM amidite described in Example 2 of US2012/0035246, the cytidine EMM amidite described in Example 3, the adenosine EMM amidite described in Example 4 and the guanosine EMM amidite described in Example 5 were used, porous glass was used as a solid-phase carrier, a high purity trichloroacetic acid toluene solution was used as a deblocking solution, 5-benzylmercapto-1H-tetrazole was used as a condensing agent, an iodine solution was used as an oxidizing agent, and a phenoxyacetic acid solution and an N-methylimidazole solution were used as a capping solution.

As a result of synthesizing the compound (A) twice, an average $OD_{260}$ of two times was 27.7 OD, and an average purity of two times was 94.0%. $OD_{260}$ represents an absorbance at UV 260 nm per 10 mm optical path length in a 1 mL solution (pH=7.5). Generally, it is known that 1 OD=40 µg in RNA, so that an average yield in two rounds is 1108 µg.

Reference Example 2

The compound (3) was produced according to the descriptions of (3) and (4) of Example (A3) of US2012/0035246 (yield: 85.5%). The compound (A) was obtained from the obtained compound (3), according to the description of Reference Example 1.

As a result of synthesizing the compound (A) twice, the average $OD_{260}$ of two times was 17.8 OD, and the average purity of two times was 93.0%. Generally, it is known that 1 OD=40 µg in RNA, so that the average yield in two rounds is 712 µg.

As can be seen from the results of Reference Example 1 and Reference Example 2, by using the compound (3) obtained by the production method of the present invention, compared with the case of using the compound (3) obtained by the conventional production method, the compound (A) is obtained in high yield.

Reference Example 3

Using the compound (3) described in Reference Example 2 and the compound (3) produced in Examples 3 to 6, the compound (A) was obtained in accordance with the description of Reference Example 1. The results are shown in Table 1 below. As can be seen from the results of Reference Example 3, by using the compound (3) obtained by the production method of the present invention, compared with the case of using the compound (3) obtained by the conventional production method, the compound (A) is obtained in high yield.

TABLE 1

| Compound (3) | Conventional method* | Example 3 | Example 4 | Example 5 | Example 6 |
|---|---|---|---|---|---|
| OD$_{269}$ | 44.5 OD | 69.6 OD | 67.4 OD | 64.8 OD | 64.3 OD |
| Yield (μg) | 1780 | 2784 | 2696 | 2593 | 2572 |

*(3) and (4) of Example (A3) of US2012/0035246

Reference Example 4

30.00 g of N-[(9H-fluoren-9-ylmethoxy)carbonyl]-L-proline and 420 mL of acetonitrile were mixed in a reaction vessel purged with nitrogen, and 32.68 g of 1-hydroxybenzotriazole was added. 9.51 g of 4-amino-1-butanol was added to the resultant mixture, 210 mL of an acetonitrile solution of 22.02 g of dicyclohexylcarbodiimide was added dropwise at room temperature, and the mixture was then stirred at room temperature for 1 hour. After completion of the reaction, the precipitate formed was removed by filtration, and the solvent of the resultant filtrate was distilled off under reduced pressure. Toluene was added to the residue and washed with a 10% aqueous sodium hydrogen carbonate solution. By distilling off the solvent of the resultant organic layer under reduced pressure, a compound represented by formula (a):

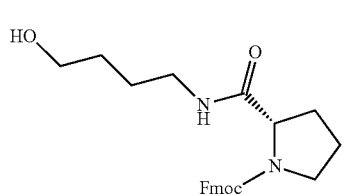

(a)

(wherein Fmoc represents a 9-fluorenylmethyloxycarbonyl group) was obtained.

90 mL of toluene was added to the total amount of the obtained compound represented by formula (a), and an azeotropic dehydration operation was carried out. 71.72 g of a toluene solution, 91 mg of N,N-dimethyl-4-aminopyridine and 50 mL of pyridine of the obtained compound represented by formula (a) were mixed, 32.64 g of 4,4'-dimethoxytrityl chloride was added at 0 to 5° C., and the mixture was then stirred at room temperature for 30 minutes under a nitrogen atmosphere. After completion of the reaction, methanol was added, and the mixture was stirred for 20 minutes. The resultant mixture was diluted with toluene and washed with a 5% aqueous sodium hydrogen carbonate solution. By distilling off the solvent of the resultant organic layer under reduced pressure, a compound represented by formula (b):

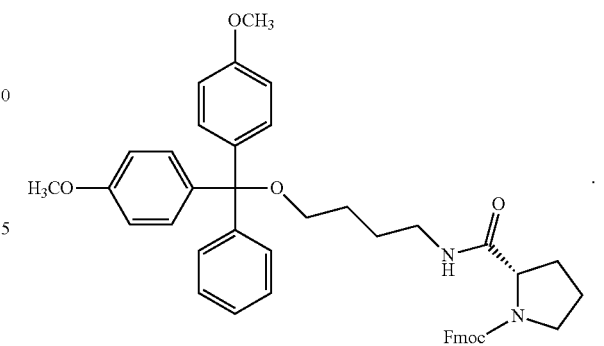

(b)

(wherein Fmoc represents a 9-fluorenylmethyloxycarbonyl group), was obtained.

After 50 mL of toluene was added to the obtained compound represented by formula (b), 59.89 g of piperidine was added dropwise at 0 to 5° C., and the mixture was then stirred at room temperature for 30 minutes under a nitrogen atmosphere. After completion of the reaction, the solvent was distilled off under reduced pressure. Toluene was added to the residue, and an azeotropic dehydration operation was carried out. The resultant residue was subjected to silica gel column chromatography (eluent ethyl acetate:methanol=80:20) to give the compound (1).

INDUSTRIAL APPLICABILITY

According to the method of the present invention, it is possible to produce the compound (3) or an enantiomer thereof capable of producing a single-stranded nucleic acid molecule capable of suppressing the expression of a target gene with high yield.

The invention claimed is:
1. A method for producing a compound represented by formula (3):

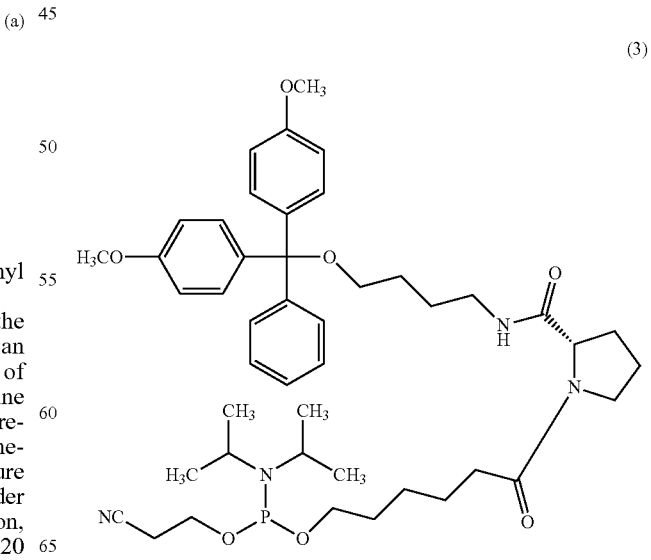

(3)

or an enantiomer thereof, comprising:
reacting a compound represented by formula (1):

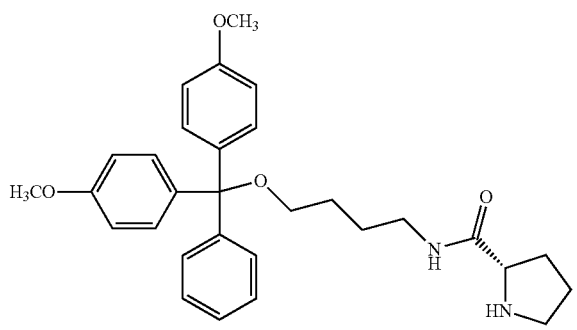

(1)

or an enantiomer thereof with 6-hydroxyhexanoic acid in a solvent in the presence of an additive and a condensing agent selected from the group consisting of 1-hydroxybenzotriazole, 1-hydroxy-7-azabenzotriazole, N-hydroxysuccinimide, ethyl(hydroxyimino)cyanoacetate, N,N'-disuccinimidyl carbonate, N-hydroxyphthalimide, N-hydroxypiperidine, 3-hydroxy-4-oxo-3,4-dihydro-1,2,3-benzotriazine and N-hydroxy-5-norbornene-2,3-dicarboxylic acid imide, and then mixing the resultant reaction mixture, water, and a base selected from the group consisting of alkali metal hydroxide, alkali metal carbonate, a bicyclic amidine compound, alkali metal alkoxide, and quaternary ammonium hydroxide to produce a compound represented by formula (2):

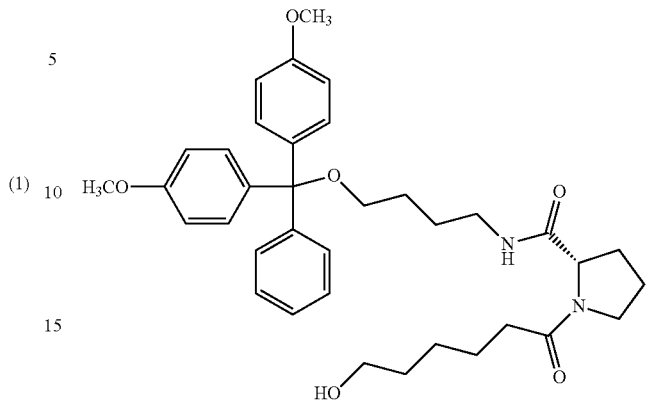

(2)

or an enantiomer thereof; and
reacting the compound represented by formula (2) and obtained in the production step or an enantiomer thereof with 2-cyanoethyl-N,N,N',N'-tetraisopropylphosphorodiamidite in a solvent in the presence of a coupling activator to obtain the compound represented by formula (3) or an enantiomer thereof.

2. The production method according to claim 1, wherein the base is an alkali metal hydroxide.

3. The production method according to claim 1, wherein the condensing agent is 1-ethyl-3-(3-dimethylaminopropyl) carbodiimide hydrochloride, 1-ethyl-3-(3-dimethylaminopropyl)carbodiimide, N,N'-dicyclohexylcarbodiimide, N,N'-diisopropylcarbodiimide, 1,1-carbonyldiimidazole, 1-propylphosphonic anhydride cyclic trimer or 2-chloro-4,6-dimethoxy-1,3,5-triazine.

4. The production method according to claim 1, wherein the additive is 1-hydroxybenzotriazole, 1-hydroxy-7-azabenzotriazole, N-hydroxysuccinimide, ethyl (hydroxyimino)cyanoacetate or N,N'-disuccinimidyl carbonate.

5. The production method according to claim 1, wherein the coupling activator is diisopropylaminetetrazole salt, 1H-tetrazole, 5-(ethylthio)-1H-tetrazole, 5-(benzylthio)-1H-tetrazole or 4,5-dicyanoimidazole.

* * * * *

UNITED STATES PATENT AND TRADEMARK OFFICE
CERTIFICATE OF CORRECTION

| | | |
|---|---|---|
| PATENT NO. | : 10,308,672 B2 | Page 1 of 1 |
| APPLICATION NO. | : 16/085330 | |
| DATED | : June 4, 2019 | |
| INVENTOR(S) | : Kanako Sato et al. | |

It is certified that error appears in the above-identified patent and that said Letters Patent is hereby corrected as shown below:

In the Claims

In Claim 1, Column 13, Lines 30 and 31:
"additive and a condensing agent" should read --additive--.

In Claim 1, Column 13, Line 37:
"acid imide," should read --acid imide, and a condensing agent,--.

In Claim 1, Column 14, Line 21:
"formula (2) and" should read --formula (2)--.

Signed and Sealed this
Fifth Day of May, 2020

Andrei Iancu
*Director of the United States Patent and Trademark Office*